US010955507B2

United States Patent
Wu et al.

(10) Patent No.: US 10,955,507 B2
(45) Date of Patent: Mar. 23, 2021

(54) MAGNETIC RESONANCE IMAGING

(71) Applicant: Shanghai Neusoft Medical Technology Co., Ltd., Shanghai (CN)

(72) Inventors: Zhigang Wu, Shenyang (CN); Ruibo Song, Shenyang (CN); Feng Huang, Shanghai (CN)

(73) Assignee: Shanghai Neusoft Medical Technology Co., Ltd., Shanghai (CN)

( * ) Notice: Subject to any disclaimer, the term of this patent is extended or adjusted under 35 U.S.C. 154(b) by 174 days.

(21) Appl. No.: 16/431,452

(22) Filed: Jun. 4, 2019

(65) Prior Publication Data
US 2019/0377049 A1 Dec. 12, 2019

(30) Foreign Application Priority Data

Jun. 6, 2018 (CN) .......................... 201810575254.4

(51) Int. Cl.
*G01R 33/561* (2006.01)
*G01R 33/565* (2006.01)
*A61B 5/055* (2006.01)

(52) U.S. Cl.
CPC .... *G01R 33/5611* (2013.01); *G01R 33/56554* (2013.01); *A61B 5/055* (2013.01)

(58) Field of Classification Search
CPC .......... G01R 33/5611; G01R 33/56554; G01R 33/565; A61B 5/055; G16H 30/20
USPC ......................................................... 324/309
See application file for complete search history.

(56) References Cited

U.S. PATENT DOCUMENTS

| 5,151,656 A | 9/1992 | Maier et al. |
| 7,492,153 B2 * | 2/2009 | Brau ................. G01R 33/5611 324/307 |

FOREIGN PATENT DOCUMENTS

| CN | 101153896 A | 4/2008 |
| CN | 106133546 A | 11/2016 |
| CN | 106137198 A | 11/2016 |
| CN | 106308798 A | 1/2017 |

OTHER PUBLICATIONS

Franciszek Hennel:"Image-Based Reduction of Artifacts in Multishot Echo-Planar Imaging", Journal of Magnetic Resonance 134,206-213 (1998), Article No. MN981502.

Michael H. Buonocore et al:"Image-Based Ghost Correction for Interleaved EPI", Magnetic Resonance in Medicine 45:96-108 (2001).

(Continued)

*Primary Examiner* — Farhana A Hoque
(74) *Attorney, Agent, or Firm* — Fish & Richardson P.C.

(57) ABSTRACT

Methods, devices, systems and apparatus for magnetic resonance imaging are provided. In an example, a method includes: obtaining M imaging data sets collected by a receiving coil array including N coil channels under M radio-frequency excitations, determining odd echo phase information and even echo phase information for each of the imaging data sets, mapping M odd echo data sets and M even echo data sets of the imaging data sets as a virtual imaging data set for a virtual coil array that includes N×M×2 virtual coil channels, and performing parallel magnetic resonance imaging based on the odd echo phase information and the even echo phase information of each of the imaging data sets, the virtual imaging data set and parallel reconstruction reference data.

20 Claims, 4 Drawing Sheets

(56) References Cited

OTHER PUBLICATIONS

Yoon-Chul Kim et al:"Automatic Correction of Echo-Planar Imaging (EPI) Ghosting Artifacts in Real-Time Interactive Cardiac MRI Using Sensitivity Encoding", Journal of Magnetic Resonance Imaging 27:239-245 (2008).

Ha-Kyu Jeong et al:"High-Resolution Human Diffusion Tensor Imaging Using 2-D Navigated Multishot SENSE EPI at 7T", Magnetic Resonance in Medicine 69:793-802 (2013).

* cited by examiner

US 10,955,507 B2

MAGNETIC RESONANCE IMAGING

CROSS REFERENCE TO RELATED APPLICATIONS

This application claims priority to Chinese Patent Application No. 201810575254.4 filed on Jun. 6, 2018, the entire content of which is incorporated herein by reference.

TECHNICAL FIELD

The present disclosure relates to a magnetic resonance imaging method and a magnetic resonance imaging apparatus in the medical imaging technology.

BACKGROUND

Magnetic Resonance Imaging (MRI) is one of main imaging methods in modern medical imageology. The basic working principle includes: hydrogen protons in a human body are excited by a radio-frequency excitation based on a magnetic resonance phenomenon, position encoding is performed with a gradient field, then a magnetic resonance signal with position information is received by using a receiving coil, and a magnetic resonance image is finally reconstructed based on Fourier Transformation.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods, devices, systems and apparatus for magnetic resonance imaging, which can improve image quality of a finally-obtained magnetic resonance image.

In general, one innovative aspect of the subject matter described in this specification can be embodied in methods that include the actions of magnetic resonance imaging, including: obtaining M imaging data sets collected by a receiving coil array under M radio-frequency excitations, where the receiving coil array includes N coil channels, a respective imaging data set obtained under each of the radio frequency excitations includes an odd echo data set and an even echo data set, and N is an integer greater than 1; for each of the imaging data sets, determining odd echo phase information of the imaging data set by performing parallel magnetic resonance imaging based on information associated with the receiving coil array and the odd echo data set in the imaging data set; determining even echo phase information of the imaging data set by performing parallel magnetic resonance imaging based on the information associated with the receiving coil array and the even echo data set in the imaging data set; mapping M odd echo data sets and M even echo data sets as a virtual imaging data set for a virtual coil array, where the virtual coil array includes N×M×2 virtual coil channels; and performing parallel magnetic resonance imaging based on the odd echo phase information and the even echo phase information of each of the imaging data sets, the virtual imaging data set and parallel reconstruction reference data.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. For example, determining the odd echo phase information of the imaging data set by performing magnetic parallel resonance imaging based on information associated with the receiving coil array and the odd echo data set in the imaging data set includes: determining an odd echo folding image for each of the N coil channels in the receiving coil array based on the odd echo data set in the imaging data set to obtain N odd echo folding images for the imaging data set; obtaining an odd echo intermediate image for the imaging data set by performing Sensitivity Encoding (SENSE) parallel resonance imaging based on coil sensitivity information of the receiving coil array and the N odd echo folding images, where the information associated with the receiving coil array includes the coil sensitivity information of the receiving coil array; obtaining a filtered odd echo intermediate image by performing low-pass filtering on the odd echo intermediate image for the imaging data set; and extracting the odd echo phase information of the imaging data set from the filtered odd echo intermediate image.

In some implementations, determining the even echo phase information of the imaging data set by performing parallel magnetic resonance imaging based on the information associated with the receiving coil array and the even echo data set in the imaging data set includes: determining an even echo folding image for each of the N coil channels in the receiving coil array based on the even echo data set in the imaging data set to obtain N even echo folding images for the imaging data set; obtaining an even echo intermediate image for the imaging data set by performing Sensitivity Encoding (SENSE) parallel magnetic resonance imaging based on coil sensitivity information of the receiving coil array and the N even echo folding images, where the information associated with the receiving coil array includes the coil sensitivity information of the receiving coil array; obtaining a filtered even echo intermediate image by performing low-pass filtering on the even echo intermediate image for the imaging data set; and extracting the even echo phase information of the imaging data set from the filtered even echo intermediate image.

In some implementations, performing parallel magnetic resonance imaging based on the odd echo phase information and the even echo phase information of each of the imaging data sets, the virtual imaging data set and the parallel reconstruction reference data includes: determining virtual coil sensitivity information of the virtual coil array based on the parallel reconstruction reference data and the number M, where the parallel reconstruction reference data includes coil sensitivity information of the receiving coil array; determining a reconstruction calculation factor of the virtual coil array based on the virtual coil sensitivity information of the virtual coil array and the odd echo phase information and the even echo phase information of each of the imaging data sets; determining an original folding image for each of the N×M×2 virtual coil channels in the virtual coil array based on the virtual imaging data set to obtain N×M×2 original folding images; and performing SENSE parallel magnetic resonance imaging based on the reconstruction calculation factor of the virtual coil array and the N×M×2 original folding images.

Obtaining the M imaging data sets collected by the receiving coil array under the M radio-frequency excitations can include: controlling magnetic resonance scanning for a subject based on an Echo Planar Imaging (EPI) sequence, where the EPI sequence includes the M radio-frequency excitations; and obtaining the M imaging data sets collected by the receiving coil array.

The actions can further include: setting a respective phase offset for each of the imaging data sets; and for each of the imaging data sets, performing phase modulation on the imaging data set using the respective phase offset to obtain a modulated imaging data set, where the modulated imaging data set includes a modulated odd echo data set and a modulated even echo data set.

In some examples, performing parallel magnetic resonance imaging based on information associated with the receiving coil array and the odd echo data set in the imaging data set includes: performing parallel magnetic resonance imaging based on the information associated with the receiving coil array and the modulated odd echo data set in the modulated imaging data set.

In some examples, performing parallel magnetic resonance imaging based on the information associated with the receiving coil array and the even echo data set in the imaging data set includes: performing parallel magnetic resonance imaging based on the information associated with the receiving coil array and the modulated even echo data set in the modulated imaging data set.

In some examples, mapping M odd echo data sets and M even echo data sets as the virtual imaging data set for the virtual coil array includes: mapping M modulated odd echo data sets and M modulated even echo data sets in the modulated imaging data sets as the virtual imaging data set for the virtual coil array.

In some implementations, determining the odd echo phase information of the image data set by performing parallel magnetic resonance imaging based on the information associated with the receiving coil array and the odd echo data set in the imaging data set includes: determining an odd echo folding images for each of the N coil channels in the receiving coil array based on the odd echo data set in the imaging data set to obtain N odd echo folding images for the imaging data set; obtaining an odd echo intermediate image for the imaging data set by performing Generalized Autocalibrating Partially Parallel Acquisitions (GRAPPA) parallel magnetic resonance imaging based on a convolution kernel for each of the N coil channels in the receiving coil array and the N odd echo folding images, where the information associate with the receiving coil array includes the convolution kernel for each of the N coil channels in the receiving coil array; obtaining a filtered odd echo intermediate image by performing low-pass filtering on the odd echo intermediate image for the imaging data set; and extracting the odd echo phase information of the imaging data set from the filtered odd echo intermediate image.

In some implementations, determining the even echo phase information of the image data set by performing parallel magnetic resonance imaging based on the information associated with the receiving coil array and the even echo data set in the imaging data set includes: determining an even echo folding image for each of the N coil channels in the receiving coil array based on the even echo data set in the imaging data set to obtain N even echo folding images for the imaging data set; obtaining an even echo intermediate image for the imaging data set by performing Generalized Autocalibrating Partially Parallel Acquisitions (GRAPPA) parallel magnetic resonance imaging based on a convolution kernel for each of the N coil channels in the receiving coil array and the N even echo folding images, where the information associate with the receiving coil array includes the convolution kernel for each of the N coil channels in the receiving coil array; obtaining a filtered even echo intermediate image by performing low-pass filtering on the even echo intermediate image for the imaging data set; and extracting the even echo phase information of the imaging data set from the filtered even echo intermediate image.

In some implementations, performing parallel magnetic resonance imaging based on the odd echo phase information and the even echo phase information of each of the imaging data sets, the virtual imaging data set, and the parallel reconstruction reference data includes: determining a convolution kernel for each of the N coil channels in the receiving coil array based on the parallel reconstruction reference data including pre-collected partial K-space data; determining a respective virtual convolution kernel for each of the N×M×2 virtual coil channels in the virtual coil array based on the convolution kernel for each of the N coil channels in the receiving coil array and the number M; determining a reconstruction calculation factor of the virtual coil array based on the virtual convolution kernel for each of the N×M×2 virtual coil channels and the odd echo phase information and the even echo phase information in each of the imaging data sets; determining a respective original folding image for each of the N×M×2 virtual coil channels in the virtual coil array based on the virtual imaging data set to obtain N×M×2 original folding images; and performing Generalized Autocalibrating Partially Parallel Acquisitions (GRAPPA) parallel magnetic resonance imaging based on the reconstruction calculation factor of the virtual coil array and the N×M×2 original folding images.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

To achieve fast magnetic resonance imaging, Echo Planar Imaging (EPI) technology may be used. That is, a magnetic resonance image of a subject may be obtained by performing magnetic resonance scanning for the subject based on an EPI sequence. In the EPI technology, after a radio-frequency excitation is performed on the subject, a gradient echo is generated during each switch based on continuous positive and negative switches of the readout gradient. If different phase encoding gradients are applied to the gradient echoes, entire K-space data may be collected by one or more excitations on the subject, that is, original imaging data of the subject may be collected. In the original imaging data, the K-space data collected at a positive readout gradient stage may be referred to as even echo data, and the K-space data collected at a negative readout gradient stage may be referred to as odd echo data.

For the EPI technology, since the readout gradient direction for the odd echo data is different from the readout gradient direction for the even echo data, different phase errors may be generated in the odd echo data and the even echo data due to the imperfection of hardware or others of a magnetic resonance imaging system, thereby causing that Nyquist artifacts (also referred to as N/2 artifacts) occurs in a finally-obtained magnetic resonance image.

To solve the above problems, the present disclosure provides a magnetic resonance imaging method and a magnetic resonance imaging apparatus to improve image quality of a finally-obtained magnetic resonance image.

Figure 1:
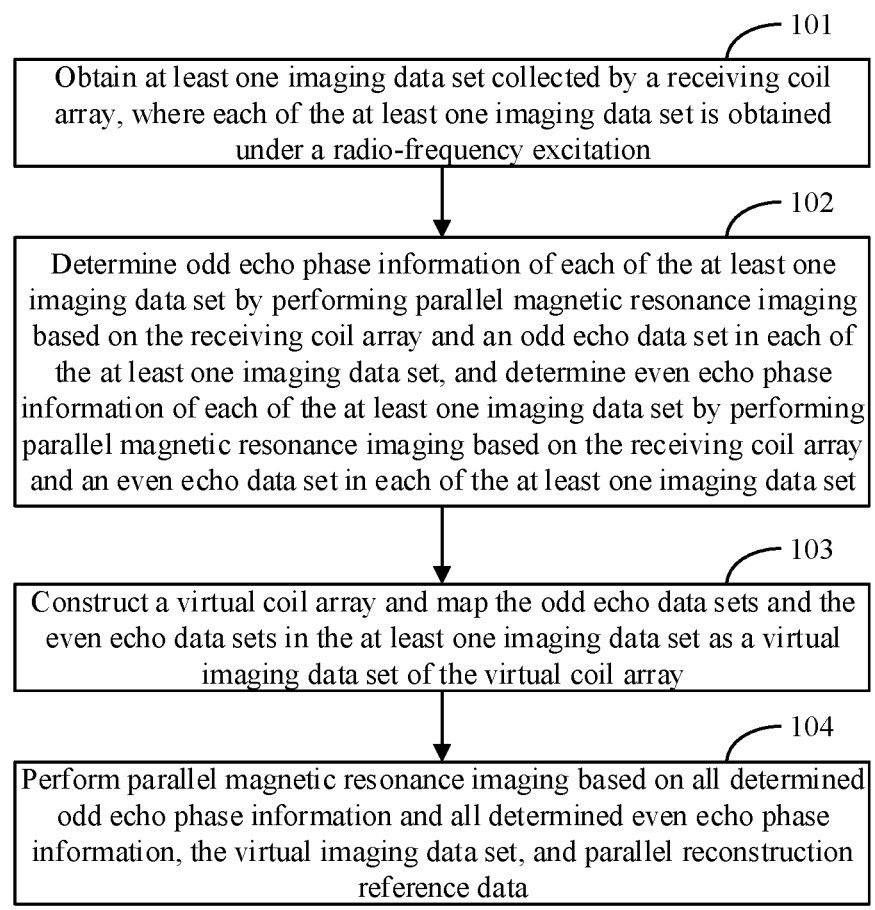
FIG. 1 is a flowchart illustrating a magnetic resonance imaging method according to an example of the present disclosure.

FIG. 1 is a flowchart illustrating a magnetic resonance imaging method according to an example of the present disclosure. The method may be applied to a computer configured to control magnetic resonance scanning for the subject in a magnetic resonance imaging system, and may include the following steps 101-104.

At step 101, at least one imaging data set collected by a receiving coil array is obtained, where each of the at least one imaging data set is obtained under a radio-frequency excitation.

In some examples, a plurality of imaging data sets collected by the receiving coil array in the magnetic resonance imaging system may be firstly obtained, where each of the imaging data sets is obtained under a radio-frequency excitation. In an example, the number of odd echo data sub-sets and the number of even echo data sub-sets in the imaging data set collected by the receiving coil array under the radio-frequency excitation are both equal to the number N of receiving coils of the receiving coil array. That is, the imaging data set obtained under the radio-frequency excitation includes an odd echo data set and an even echo data set, where the odd echo data set includes N odd echo data sub-sets and the even echo data set includes N even echo data sub-sets.

For example, if the receiving coil array in the magnetic resonance imaging system includes 16 receiving coils (hereinafter also referred to as coil channels), the receiving coil array may collect 16 odd echo data sub-sets and 16 even echo data sub-sets through the 16 coil channels under a radio-frequency excitation, where different odd echo data sub-sets correspond to different coil channels respectively, and different even echo data sub-sets also correspond to different coil channels respectively.

In a practical application, the computer in the magnetic resonance imaging system may control the magnetic resonance scanning for the subject based on the EPI sequence. At this case, the EPI sequence used for the magnetic resonance scanning includes at least one radio-frequency excitation. The subject may generate one imaging data set under one radio-frequency excitation, and the computer may obtain the imaging data set collected by the receiving coil array. In an example, if the EPI sequence used for the magnetic resonance scanning includes only one radio-frequency excitation, the computer obtains only one imaging data set collected by the receiving coil array; and if the EPI sequence used for magnetic resonance scanning includes a plurality of radio-frequency excitations, the computer obtains a plurality of imaging data sets collected by the receiving coil array.

At step 102, odd echo phase information of each of the at least one imaging data set is determined by performing parallel magnetic resonance imaging based on the receiving coil array and an odd echo data set in each of the at least one imaging data set, and even echo phase information of each of the at least one imaging data set is determined by performing parallel magnetic resonance imaging based on the receiving coil array and an even echo data set in each of the at least one imaging data set.

In some examples, after at least one imaging data set is obtained, each of the at least one imaging data set may be firstly divided into the odd echo data set including N odd echo data sub-sets and the even echo data set including N even echo data sub-sets. N refers to the number of coil channels in the receiving coil array. Further, in the imaging data set, different odd echo data sub-sets correspond to different coil channels respectively, and different even echo data sub-sets also correspond to different coil channels respectively.

Subsequently, the odd echo phase information of each of the imaging data sets may be determined based on the above receiving coil array and the odd echo data set in each of the imaging data sets; meanwhile, the even echo phase information of each of the imaging data sets may also be determined based on the receiving coil array and the even echo data set in each of the imaging data sets.

Figure 2:
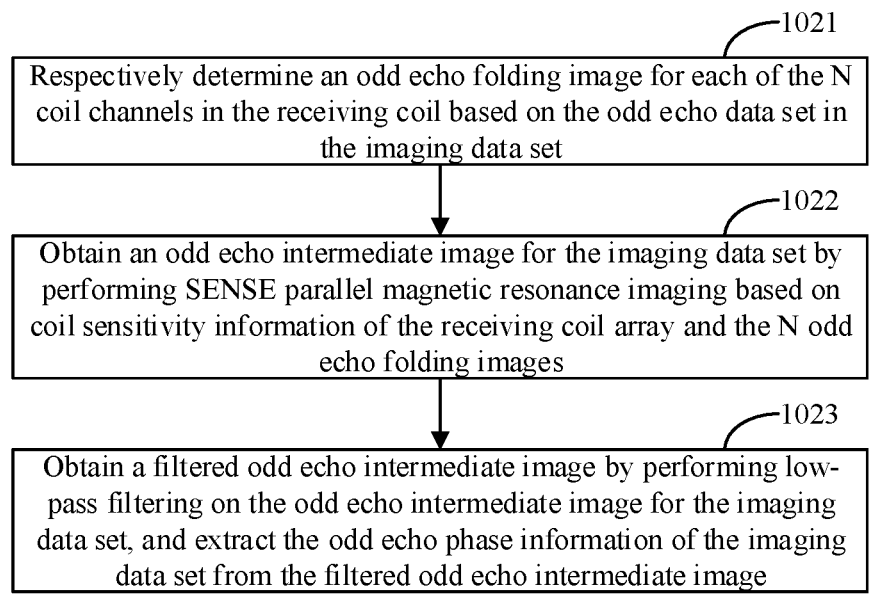
FIG. 2 is a flowchart illustrating a magnetic resonance imaging method according to another example of the present disclosure.

As shown in FIG. 2, with a Sensitivity Encoding (SENSE) algorithm for performing parallel magnetic resonance imaging as an example, the odd echo phase information of each of the imaging data set may be determined by performing parallel magnetic resonance imaging based on the receiving coil array and the odd echo data set in each of the imaging data sets through the following steps 1021-1023. At steps 1021-1023, one of the imaging data sets is taken as an example to illustrate the determination of the odd echo phase information of the imaging data set.

At step 1021, an odd echo folding image for each of the N coil channels in the receiving coil is respectively determined based on the odd echo data set in the imaging data set.

At step 1022, an odd echo intermediate image for the imaging data set is obtained by performing SENSE parallel magnetic resonance imaging based on coil sensitivity information of the receiving coil array and the N odd echo folding images.

At step 1023, a filtered odd echo intermediate image is obtained by performing low-pass filtering on the odd echo intermediate image for the imaging data set, and the odd echo phase information of the imaging data set is extracted from the filtered odd echo intermediate image.

In some examples, for one of the imaging data sets, after the odd echo data set is separated from the imaging data set, since different odd echo data sub-sets in the odd echo data set correspond to different coil channels respectively, the odd echo folding image for each of the N coil channels in the above receiving coil array may be respectively determined based on the N odd echo data sub-sets. In a practical application, the odd echo folding image for one of the coil channels may be obtained by performing Fast Fourier Transformation (FFT) calculation for the odd echo data sub-set for the coil channel.

After the odd echo folding image for each of the coil channels is obtained respectively, SENSE parallel magnetic resonance imaging may be performed based on coil sensitivity information of the receiving coil array and N odd echo folding images to obtain an odd echo intermediate image for the imaging data set. The coil sensitivity information of the receiving coil array may be obtained by pre-measurement. In an example, the coil sensitivity information of the receiving coil array is a matrix of N rows and P columns, where N refers to the number of coil channels of the receiving coil array, and P refers to the number of image pixel points. In some examples, the odd echo intermediate image for the imaging data set may be obtained based on the following formula (1).

$$\begin{bmatrix} S_1(r_1) & \cdots & S_1(r_p) \\ \vdots & \ddots & \vdots \\ S_N(r_1) & \cdots & S_N(r_p) \end{bmatrix} \times I_{odd} = \begin{bmatrix} I_{fold,1}(r_1) & \cdots & I_{fold,1}(r_p) \\ \vdots & \ddots & \vdots \\ I_{fold,N}(r_1) & \cdots & I_{fold,N}(r_p) \end{bmatrix}. \quad (1)$$

In the above formula (1), $S_N(r_P)$ refers to sensitivity of the N-th coil channel in the receiving coil array at the P-th image pixel point, $I_{fold,N}(r_P)$ refers to information of the P-th image pixel point on the odd echo folding image for the N-th coil channel in the receiving coil array, and $I_{odd}$ refers to the odd echo intermediate image for the imaging data set.

It may be understood that for any one of the imaging data sets, the odd echo intermediate image for the imaging data set may be obtained in the above manner. After the odd echo intermediate image for the imaging data set is obtained, low-pass filtering may be firstly performed on the odd echo intermediate image for the imaging data set, so as to increase a signal-to-noise ratio of the odd echo intermediate image. Since the filtered odd echo intermediate image includes not only amplitude information at each image pixel point, but also phase information at each image pixel point, the phase information may be directly extracted from the filtered odd echo intermediate image, so as to determine the odd echo phase information for the imaging data set.

Correspondingly, the even echo phase information of each imaging data set may be determined by performing parallel magnetic resonance imaging based on the receiving coil array and the even echo data set in each of the imaging data sets through the following steps. At the following steps, take one of the imaging data sets as an example to illustrate the determination of the even echo phase information of the imaging data set.

First, an even echo folding image for each of N coil channels in the receiving coil array is respectively determined based on the even echo data set in the imaging data set.

Then, an even echo intermediate image for the imaging data set is obtained by performing SENSE parallel magnetic resonance imaging based on the coil sensitivity information of the receiving coil array and the N even echo folding images.

Finally, a filtered even echo intermediate image is obtained by performing low-pass filtering on the even echo intermediate image for the imaging data set, and the even echo phase information of the imaging data set is extracted from the filtered even echo intermediate image.

The implementation of the above steps may be referred to the descriptions of the above steps 1021-1023, which will not be described herein.

After the odd echo phase information and the even echo phase information of each of the imaging data sets are determined, the odd echo phase information and the even echo phase information may be used for subsequent parallel magnetic resonance reconstruction, that is, a phase difference between odd echo data and even echo data is calibrated by using the odd echo phase information and the even echo phase information.

At step 103, a virtual coil array is constructed, and the odd echo data sets and the even echo data sets in the at least one imaging data set are mapped as a virtual imaging data set of the virtual coil array.

In some examples, after the at least one imaging data set is obtained, the virtual coil array may be constructed, and the odd echo data sets and the even echo data sets in the at least one imaging data set are mapped as the virtual imaging data set of the virtual coil array.

Figure 3:
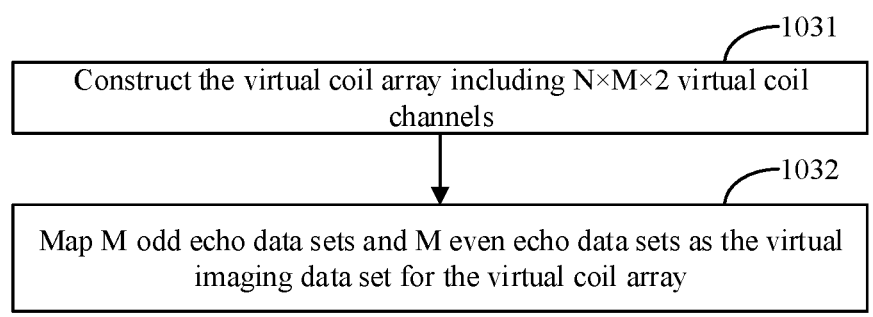
FIG. 3 is a flowchart illustrating a magnetic resonance imaging method according to still another example of the present disclosure.

In some example, if the receiving coil array in the magnetic resonance imaging system includes N coil channels and the computer in the magnetic resonance imaging system obtains M imaging data sets collected by the receiving coil array, each of the imaging data sets includes N odd echo data sub-sets and N even echo data sub-sets, where N is an integer greater than 1, and M refers to the number of excitations. In this case, as shown in FIG. 3, according to the following steps 1031-1032, the virtual coil array may be constructed, and the at least one imaging data set may be mapped as the virtual imaging data set of the virtual coil array.

At step 1031, the virtual coil array including N×M×2 virtual coil channels is constructed.

At step 1032, M odd echo data sets and M even echo data sets are mapped as the virtual imaging data set for the virtual coil array.

M imaging data sets collected by the receiving coil array include M odd echo data sets and M even echo data sets, where M odd echo data sets include N×M odd echo data sub-sets, and M even echo data sets include N×M even echo data sub-sets. Therefore, the virtual coil array including N×M×2 virtual coil channels may be constructed, and the N×M odd echo data sub-sets and the N×M even echo data sub-sets (totally N×M×2 data sub-sets) may be mapped as the virtual imaging data set for the virtual coil array.

Continuing the example at the above step 101, if the computer in the magnetic resonance imaging system totally obtains 10 imaging data sets collected by the above receiving coil array and each of the imaging data sets includes 16 odd echo data sub-sets and 16 even echo data sub-sets, the virtual coil array may be constructed, and a total of 160 odd echo data sub-sets and 160 even echo data sub-sets collected by the receiving coil array may be mapped as the virtual imaging data set for the virtual coil array. In an example, the virtual coil array including 320 virtual coil channels is constructed, and a total of 320 data sub-sets are mapped as the virtual imaging data set collected by the virtual coil array through 320 virtual coil channels under one radio-frequency excitation.

At step 104, parallel magnetic resonance imaging is performed based on all determined odd echo phase information and all determined even echo phase information, the virtual imaging data set, and parallel reconstruction reference data.

In some examples, after the virtual coil array is constructed, parallel magnetic resonance imaging may be performed based on all odd echo phase information and all even echo phase information which are determined at the above step 102, the virtual imaging data set and the parallel reconstruction reference data, so as to obtain a final magnetic resonance image of the subject.

Figure 4:
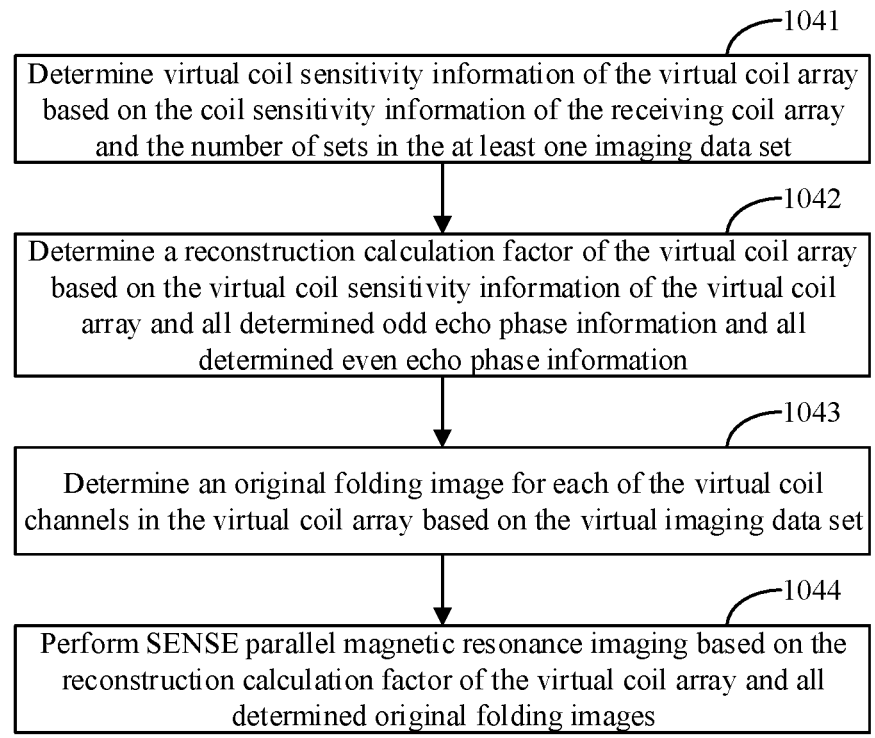
FIG. 4 is a flowchart illustrating a magnetic resonance imaging method according to yet another example of the present disclosure.

As show in FIG. 4, with the SENSE algorithm to perform parallel magnetic resonance imaging as an example, the parallel magnetic resonance imaging may be performed based on all determined odd echo phase information and all determined even echo phase information, the virtual imaging data set, and the parallel reconstruction reference data through the following steps 1041-1044.

At step 1041, virtual coil sensitivity information of the virtual coil array is determined based on the coil sensitivity information of the receiving coil array and the number of sets in the at least one imaging data set.

At step 1042, a reconstruction calculation factor of the virtual coil array is determined based on the virtual coil sensitivity information of the virtual coil array and all determined odd echo phase information and all determined even echo phase information.

At step 1043, an original folding image for each of the virtual coil channels in the virtual coil array is determined based on the virtual imaging data set.

At step 1044, SENSE parallel magnetic resonance imaging is performed based on the reconstruction calculation factor of the virtual coil array and all determined original folding images.

In some examples, after the virtual coil array is constructed, the virtual coil sensitivity information of the virtual coil array may be determined based on the coil sensitivity information of the receiving coil array in the magnetic resonance imaging system and the number of sets in the obtained imaging data sets. At this case, the coil sensitivity information of the receiving coil array in the magnetic resonance imaging system is the parallel reconstruction reference data.

In some examples, after the virtual coil array including N×M×2 virtual coil channels is constructed, the coil sensitivity information of the receiving coil array including N coil channels may be extended into a matrix of N×M×2 rows and P columns as the virtual coil sensitivity information of the virtual coil array. If the coil sensitivity information of the receiving coil array is $$\begin{bmatrix} S_1(r_1) & \ldots & S_1(r_p) \\ \vdots & \ddots & \vdots \\ S_N(r_1) & \ldots & S_N(r_p) \end{bmatrix},$$

the virtual coil sensitivity information of the virtual coil array obtained by extension is $$\begin{bmatrix} S_1(r_1) & \ldots & S_1(r_p) \\ \vdots & \ddots & \vdots \\ S_N(r_1) & \ldots & S_N(r_p) \\ & \ddots & \\ & & \ddots \\ & & & \ddots \\ S_1(r_1) & \ldots & S_1(r_p) \\ \vdots & \ddots & \vdots \\ S_N(r_1) & \ldots & S_N(r_p) \end{bmatrix},$$

where the first to N-th rows of the virtual coil sensitivity information of the virtual coil array is formed by the coil sensitivity information of the receiving coil array, the (N+1)-th to 2N-th rows of the virtual coil sensitivity information of the virtual coil array is also formed by the coil sensitivity information of the receiving coil array, and so on.

After the virtual coil sensitivity information of the virtual coil array is determined, the reconstruction calculation factor of the virtual coil array may be determined based on the virtual coil sensitivity information of the virtual coil array and all determined odd echo phase information and all determined even echo phase information. In an example, the reconstruction calculation factor of the virtual coil array may be determined based on the following formula (2).

$$X = \begin{bmatrix} S_1(r_1) & \ldots & S_1(r_p) \\ \vdots & \ddots & \vdots \\ S_N(r_1) & \ldots & S_N(r_p) \\ S_1(r_1) & \ldots & S_1(r_p) \\ \vdots & \ddots & \vdots \\ S_N(r_1) & \ldots & S_1(r_p) \\ & \ddots & \\ & & \ddots \\ & & & \ddots \\ S_1(r_1) & \ldots & S_1(r_p) \\ \vdots & \ddots & \vdots \\ S_N(r_1) & \ldots & S_1(r_p) \\ S_1(r_1) & \ldots & S_1(r_p) \\ \vdots & \ddots & \vdots \\ S_N(r_1) & \ldots & S_N(r_p) \end{bmatrix} \times \begin{bmatrix} P_{fold,odd,1,1}(r_1) & \ldots & P_{fold,odd,1,1}(r_p) \\ \vdots & \ddots & \vdots \\ P_{fold,odd,N,1}(r_1) & \ldots & P_{fold,odd,N,1}(r_p) \\ P_{fold,even,1,1}(r_1) & \ldots & P_{fold,even,1,1}(r_p) \\ \vdots & \ddots & \vdots \\ P_{fold,even,N,1}(r_1) & \ldots & P_{fold,even,N,1}(r_p) \\ & \ddots & \\ & & \ddots \\ & & & \ddots \\ P_{fold,odd,1,M}(r_1) & \ldots & P_{fold,odd,1,M}(r_p) \\ \vdots & \ddots & \vdots \\ P_{fold,odd,N,M}(r_1) & \ldots & P_{fold,odd,N,M}(r_p) \\ P_{fold,even,1,M}(r_1) & \ldots & P_{fold,even,1,M}(r_p) \\ \vdots & \ddots & \vdots \\ P_{fold,even,N,M}(r_1) & \ldots & P_{fold,even,N,M}(r_p) \end{bmatrix} \quad (2)$$

In the above formula (2), $P_{fold,odd,N,M}(r_P)$ refers to phase information of the P-th image pixel point on the odd echo folding image for the N-th coil channel in the M-th imaging data set, and $P_{fold,even,N,M}(r_P)$ refers to phase information of the P-th image pixel point on the even echo folding image for the N-th coil channel in the M-th imaging data set.

In some examples, the original folding image for each of the virtual coil channels in the virtual coil array may be determined based on the virtual imaging data set. The virtual imaging data set includes N×M odd echo data sub-sets and N×M even echo data sub-sets, therefore, N×M odd echo folding images may be obtained by performing FFT calculation on N×M odd echo data sub-sets in the virtual coil array, and N×M even echo folding images may be obtained by performing FFT calculation on N×M even echo data sub-sets in the virtual coil array.

It is noted that to reduce a calculation amount and lower a calculation complexity, the N×M odd echo folding images and the N×M even echo folding images which are determined based on the odd echo data set and the even echo data set in each of the imaging data sets at the above step 1021 and step 1024 may also be directly taken as the original folding image for each of the virtual coil channels in the virtual coil array.

Subsequently, the final magnetic resonance image of the subject may be obtained by performing SENSE parallel magnetic resonance imaging based on the reconstruction calculation factor of the virtual coil array and all determined original folding images. In an example, SENSE parallel magnetic resonance imaging may be performed based on the following formula (3).

$$X \times I_{EPI} = \begin{bmatrix} I_{fold,odd,1,1}(r_1) & \cdots & I_{fold,odd,1,1}(r_p) \\ \vdots & \ddots & \vdots \\ I_{fold,odd,N,1}(r_1) & \cdots & I_{fold,odd,N,1}(r_p) \\ I_{fold,even,1,1}(r_1) & \cdots & I_{fold,even,1,1}(r_p) \\ \vdots & \ddots & \vdots \\ I_{fold,even,N,1}(r_1) & \cdots & I_{fold,even,N,1}(r_p) \\ & \ddots & \\ & \ddots & \\ & \ddots & \\ I_{fold,odd,1,M}(r_1) & \cdots & I_{fold,odd,1,M}(r_p) \\ \vdots & \ddots & \vdots \\ I_{fold,odd,N,M}(r_1) & \cdots & I_{fold,odd,N,M}(r_p) \\ I_{fold,even,1,M}(r_1) & \cdots & I_{fold,even,1,M}(r_p) \\ \vdots & \ddots & \vdots \\ I_{fold,even,N,M}(r_1) & \cdots & I_{fold,even,N,M}(r_p) \end{bmatrix} \quad (3)$$

In the above formula (3), $I_{fold,odd,N,M}(r_P)$ refers to information of the P-th image pixel point on the odd echo folding image for the N-th coil channel in the M-th imaging data set, and $I_{fold,even,N,M}(r_P)$ refers to information of the P-th image pixel point on the even echo folding image for the N-th coil channel in the M-th imaging data set.

It is noted that the magnetic resonance imaging method provided by the present disclosure is not only applied to SENSE imaging technology, but also applied to the parallel magnetic resonance imaging technology, such as Generalized Autocalibrating Partially Parallel Acquisitions (GRAPPA) technology. It is noted that the parallel reconstruction reference data depends on the parallel magnetic resonance imaging technology. For example, when parallel magnetic resonance imaging is performed based on a GRAPPA algorithm, the parallel reconstruction reference data is pre-collected reference data. The pre-collected reference data refers to pre-collected partial K-space data, such as data in a central region of a K-space.

When the magnetic resonance imaging method provided by the present disclosure is performed based on the GRAPPA algorithm, performing parallel magnetic resonance imaging based on the odd echo phase information and the even echo phase information of each of the imaging data sets, the virtual imaging data set, and the parallel reconstruction reference data includes: determining a convolution kernel for each of the coil channels in the receiving coil array based on the parallel reconstruction reference data; determining a virtual convolution kernel for each of the virtual coil channels in the virtual coil array based on the convolution kernel for each of the coil channels in the receiving coil array and the number M; determining the reconstruction calculation factor of the virtual coil array based on the virtual convolution kernel for each of the virtual coil channels and the odd echo phase information and the even echo phase information of each of the imaging data sets; determining an original folding image for each of the N×M×2 virtual coil channels in the virtual coil array based on the virtual imaging data set; and performing GRAPPA parallel magnetic resonance imaging based on the reconstruction calculation factor of the virtual coil array and the N×M×2 original folding images.

The above steps are similar to the steps for performing the magnetic resonance imaging method based on the SENSE algorithm provided by the present disclosure, thus, similar parts will not be described herein.

In an example, for each of the imaging data sets, an odd echo folding image for each of the N coil channels in the receiving coil array is determined based on the odd echo data set in the imaging data set; the odd echo intermediate image for the imaging data set is obtained by performing GRAPPA parallel magnetic resonance imaging based on the convolution kernel for each of the coil channels in the receiving coil array and the N odd echo folding images; a filtered odd echo intermediate image is obtained by performing low-pass filtering on the odd echo intermediate image for the imaging data set; and the odd echo phase information of the imaging data set is extracted from the filtered odd echo intermediate image.

In an example, an even echo folding image for each of the N coil channels in the receiving coil array is determined based on the even echo data set in the imaging data set; the even echo intermediate image for the imaging data set is obtained by performing GRAPPA parallel magnetic resonance imaging based on a convolution kernel for each of the coil channels in the receiving coil array and the N even echo folding images; a filtered even echo intermediate image is obtained by performing low-pass filtering on the even echo intermediate image for the imaging data set; and the even echo phase information of the imaging data set is extracted from the filtered even echo intermediate image.

It can be seen from the above examples that after a plurality of imaging data sets are obtained under a plurality of radio-frequency excitations in the EPI sequence, odd echo phase information and even echo phase information of each of the imaging data sets may be determined by respectively performing parallel reconstruction on the odd echo data set and the even echo data set in each of the imaging data sets. Subsequently, the virtual coil array may be constructed, and all odd echo data sub-sets and all even echo data sub-sets may be mapped as the virtual imaging data set for the virtual coil array. Finally, the final magnetic resonance image may be obtained by performing parallel magnetic resonance imaging based on all odd echo phase information, all even echo phase information, the virtual imaging data set, and parallel reconstruction reference data. In this case, since the determined odd echo phase information and the determined even echo phase information are used for the subsequent parallel magnetic resonance reconstruction, that is, calibration is performed on a phase difference between the odd echo data and the even echo data based on the determined odd echo phase information and the determined even echo phase information, N/2 artifacts are avoided. In addition, it may be considered that the number of coil channels in a coil array is increased in a practical application, and thus a geometric factor (g-factor) may be effectively decreased, that is, the impact of the g-factor on the finally magnetic resonance image is decreased. It is noted that a larger geometric factor means a lower signal-to-noise ratio. Therefore, by the magnetic resonance imaging provided in the present disclosure, the signal-to-noise ratio of the finally magnetic resonance image is increased and the related artifacts in the finally magnetic resonance image are decreased, thereby improving the image quality of the finally magnetic resonance image.

It is noted that to further increase independence between different coil channels of the virtual coil array and avoid excessive overlapped pixels at a particular position, in an example, based on a preset phase modulation rule, under each radio-frequency excitation, phase modulation is performed on the collected imaging data set. The phase modulation rule may include different phase offsets set for the imaging data set obtained under each radio-frequency excitation. For example, the phase offset for the imaging data set obtained under the first radio-frequency excitation is 10°, the phase offset for the imaging data set obtained under the second radio-frequency excitation is 20°, and so on. In some examples, imaging data at different positions of the K-space is collected under each radio-frequency excitation, so that the imaging data collected under different radio-frequency excitations have different phase offsets, that is, different imaging data sets have different phase offsets. Subsequently, the parallel magnetic resonance imaging may be performed by using the phase-modulated imaging data.

Corresponding to the above examples of the magnetic resonance imaging methods, the present disclosure also provides examples of a magnetic resonance imaging apparatus.

Figure 5:
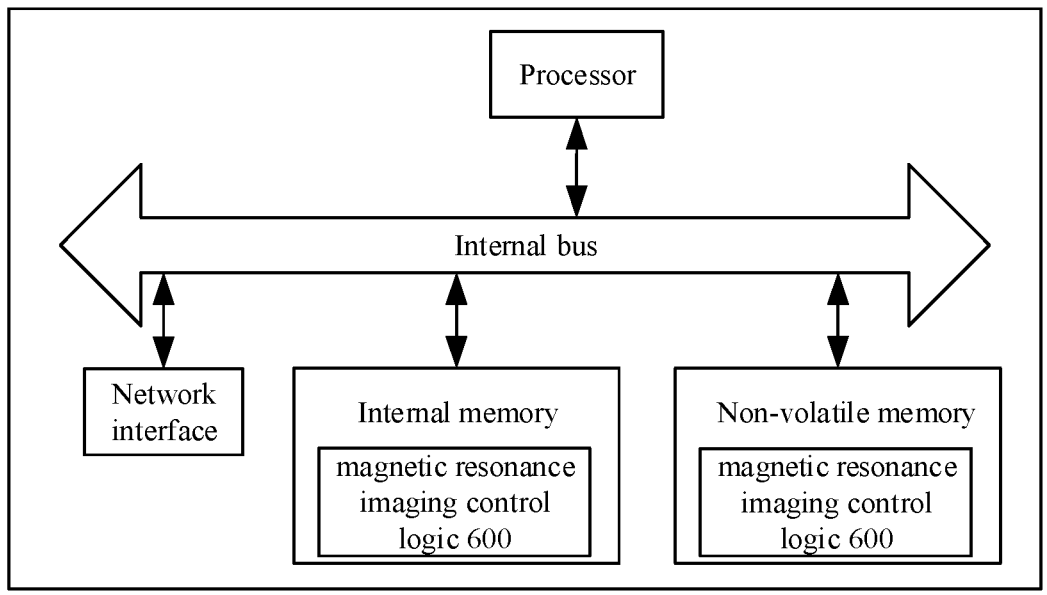
FIG. 5 is a schematic diagram illustrating a hardware structure of a magnetic resonance imaging apparatus according to an example of the present disclosure.

The magnetic resonance imaging apparatus provided by the present disclosure may be applied to the magnetic resonance imaging system. The apparatus example may be implemented by software, or may also be implemented by hardware or a combination of software and hardware. FIG. 5 is a schematic diagram illustrating a hardware structure of a magnetic resonance imaging apparatus according to an example of the present disclosure. The magnetic resonance imaging apparatus may also include another hardware according to an actual function of magnetic resonance imaging in addition to a processor, an internal memory, a network interface, and a non-volatile memory as shown in FIG. 5, which is not described herein.

Figure 6:
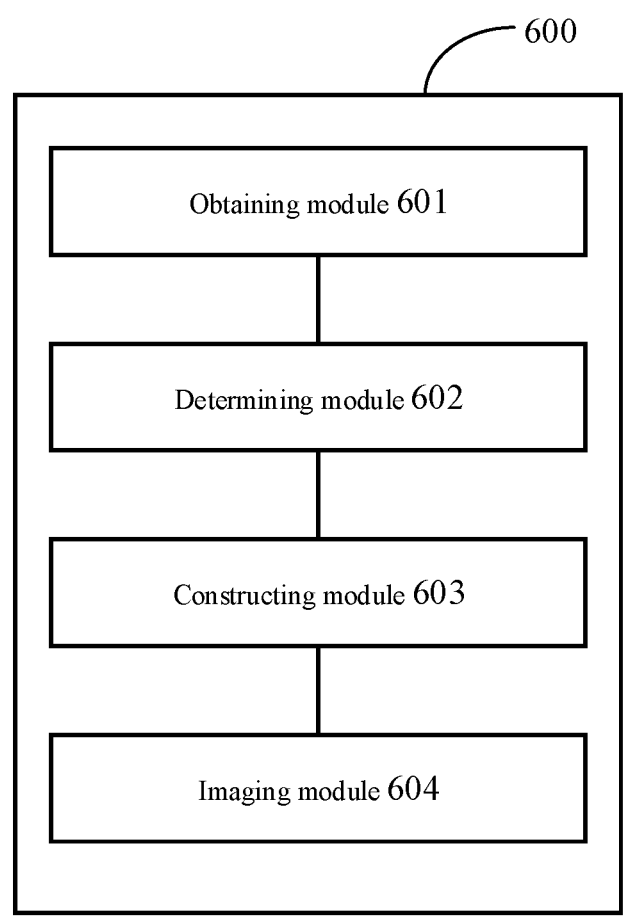
FIG. 6 is a block diagram illustrating a control logic for magnetic resonance imaging according to an example of the present disclosure.

FIG. 6 is a block diagram illustrating a control logic 600 for magnetic resonance imaging according to an example of the present disclosure. The control logic 600 may be applied to the magnetic resonance imaging apparatus as shown in FIG. 5 and stored in the non-volatile memory, and the magnetic resonance imaging system may also include a receiving coil array. The control logic 600 may include: an obtaining module 601, configured to obtain M imaging data sets collected by a receiving coil array under M radio-frequency excitations, where the receiving coil array includes N coil channels, the imaging data set obtained under any one of the radio frequency excitations comprises an odd echo data set and an even echo data set, and N is an integer greater than 1; a determining module 602, configured to for each of the imaging data sets, determine odd echo phase information of the imaging data set by performing parallel magnetic resonance imaging based on the receiving coil array and the odd echo data set in the imaging data set, and for each of the imaging data sets, determine even echo phase information of the imaging data set by performing parallel magnetic resonance imaging based on the receiving coil array and the even echo data set in the imaging data set; a constructing module 603, configured to construct a virtual coil array and map M odd echo data sets and M even echo data sets as a virtual imaging data set for the virtual coil array, where the virtual coil array includes N×M×2 virtual coil channels; and an imaging module 604, configured to perform parallel magnetic resonance imaging based on the odd echo phase information and the even echo phase information of each of the imaging data sets, the virtual imaging data set and parallel reconstruction reference data.

How the magnetic resonance imaging apparatus executes the control logic 600 will be further described with a software implementation as an example. In this example, the control logic 600 of the present disclosure is understood as computer instructions stored in a non-volatile memory. When a processor on the magnetic resonance imaging apparatus of the present disclosure executes the control logic 600, the processor may perform the above magnetic resonance imaging method by invoking the instructions for the control logic 600 stored on the non-volatile memory.

The present disclosure also provides a non-volatile machine readable storage medium storing machine executable instructions, where one or more processors are caused by the machine executable instructions to perform the above magnetic resonance imaging method.

Details of the implementation process of the functions and effects of different modules in the above logic may refer to the implementation process of corresponding steps in the above method, which will not be described herein.

Since the apparatus examples and the storage medium examples substantially correspond to the method examples, the related part refers to part of the descriptions of the method examples. The apparatus examples described above are merely illustrative, where the units described as separate members may be or not be physically separated, and the members displayed as units may be or not be physical units, i.e., may be located in one place, or may be distributed to a plurality of network units. Part or all of the modules may be selected according to actual requirements to implement the objectives of the solutions in the examples. Those of ordinary skill in the art may understand and carry out them without creative work.

Examples described in detail are here with the examples thereof expressed in the drawings. Where the above descriptions involve the drawings, like numerals in different drawings refer to like or similar elements unless otherwise indicated. The embodiments described in the examples do not represent all embodiments consistent with the present disclosure. Rather, they are merely examples of apparatuses and methods consistent with some aspects of the present disclosure as detailed in the appended claims.

The term used in the present disclosure is for the purpose of describing examples only and is not intended to limit the present disclosure. As used in this disclosure and the appended claims, the singular forms "a", "an" and "the" are intended to include the plural forms as well, unless the context clearly indicates otherwise. It should also be understood that the term "and/or" as used herein refers to and includes any and all possible combinations of one or more of the associated listed items.

It shall be understood that, although the terms "first," "second," "third," and the like may be used herein to describe various information, the information should not be limited by these terms. These terms are only used to distinguish one category of information from another. For example, without departing from the scope of the present disclosure, first information may be referred as second information; and similarly, second information may also be referred as first information. As used herein, the term "if" may be interpreted as "when" or "upon" or "in response to determining" depending on the context.

The foregoing descriptions are only examples of the present disclosure but not intended to limit the present disclosure. Any modifications, equivalent substitutions, and improvements made within the spirit and principles of the disclosure shall be encompassed in the scope of protection of the present disclosure.

What is claimed is:

1. A magnetic resonance imaging method, comprising:
    obtaining M imaging data sets collected by a receiving coil array under M radio-frequency excitations, wherein the receiving coil array comprises N coil channels, a respective imaging data set obtained under each of the radio frequency excitations comprises an odd echo data set and an even echo data set, and N is an integer greater than 1;
    for each of the imaging data sets,
        determining odd echo phase information of the imaging data set by performing parallel magnetic resonance imaging based on information associated with the receiving coil array and the odd echo data set in the imaging data set;
        determining even echo phase information of the imaging data set by performing parallel magnetic resonance imaging based on the information associated with the receiving coil array and the even echo data set in the imaging data set;
    mapping M odd echo data sets and M even echo data sets as a virtual imaging data set for a virtual coil array, wherein the virtual coil array comprises N×M×2 virtual coil channels; and
    performing parallel magnetic resonance imaging based on the odd echo phase information and the even echo phase information of each of the imaging data sets, the virtual imaging data set and parallel reconstruction reference data.

2. The method of claim 1, wherein determining the odd echo phase information of the imaging data set by performing magnetic parallel resonance imaging based on information associated with the receiving coil array and the odd echo data set in the imaging data set comprises:
    determining an odd echo folding image for each of the N coil channels in the receiving coil array based on the odd echo data set in the imaging data set to obtain N odd echo folding images for the imaging data set;
    obtaining an odd echo intermediate image for the imaging data set by performing Sensitivity Encoding (SENSE) parallel resonance imaging based on coil sensitivity information of the receiving coil array and the N odd echo folding images, wherein the information associated with the receiving coil array comprises the coil sensitivity information of the receiving coil array;
    obtaining a filtered odd echo intermediate image by performing low-pass filtering on the odd echo intermediate image for the imaging data set; and
    extracting the odd echo phase information of the imaging data set from the filtered odd echo intermediate image.

3. The method of claim 1, wherein determining the even echo phase information of the imaging data set by performing parallel magnetic resonance imaging based on the information associated with the receiving coil array and the even echo data set in the imaging data set comprises:
    determining an even echo folding image for each of the N coil channels in the receiving coil array based on the even echo data set in the imaging data set to obtain N even echo folding images for the imaging data set;
    obtaining an even echo intermediate image for the imaging data set by performing Sensitivity Encoding (SENSE) parallel magnetic resonance imaging based on coil sensitivity information of the receiving coil array and the N even echo folding images, wherein the information associated with the receiving coil array comprises the coil sensitivity information of the receiving coil array;
    obtaining a filtered even echo intermediate image by performing low-pass filtering on the even echo intermediate image for the imaging data set; and
    extracting the even echo phase information of the imaging data set from the filtered even echo intermediate image.

4. The method of claim 1, wherein performing parallel magnetic resonance imaging based on the odd echo phase information and the even echo phase information of each of the imaging data sets, the virtual imaging data set and the parallel reconstruction reference data comprises:
    determining virtual coil sensitivity information of the virtual coil array based on the parallel reconstruction reference data and the number M, wherein the parallel reconstruction reference data comprises coil sensitivity information of the receiving coil array;
    determining a reconstruction calculation factor of the virtual coil array based on the virtual coil sensitivity information of the virtual coil array and the odd echo phase information and the even echo phase information of each of the imaging data sets;
    determining an original folding image for each of the N×M×2 virtual coil channels in the virtual coil array based on the virtual imaging data set to obtain N×M×2 original folding images; and
    performing SENSE parallel magnetic resonance imaging based on the reconstruction calculation factor of the virtual coil array and the N×M×2 original folding images.

5. The method of claim 1, wherein obtaining the M imaging data sets collected by the receiving coil array under the M radio-frequency excitations comprises:
    controlling magnetic resonance scanning for a subject based on an Echo Planar Imaging (EPI) sequence, wherein the EPI sequence comprises the M radio-frequency excitations; and
    obtaining the M imaging data sets collected by the receiving coil array.

6. The method of claim 1, further comprising:
    setting a respective phase offset for each of the imaging data sets; and
    for each of the imaging data sets, performing phase modulation on the imaging data set using the respective phase offset to obtain a modulated imaging data set, wherein the modulated imaging data set comprises a modulated odd echo data set and a modulated even echo data set.

7. The method of claim 6, wherein performing parallel magnetic resonance imaging based on information associated with the receiving coil array and the odd echo data set in the imaging data set comprises:
    performing parallel magnetic resonance imaging based on the information associated with the receiving coil array and the modulated odd echo data set in the modulated imaging data set.

8. The method of claim 6, wherein performing parallel magnetic resonance imaging based on the information associated with the receiving coil array and the even echo data set in the imaging data set comprises:
performing parallel magnetic resonance imaging based on the information associated with the receiving coil array and the modulated even echo data set in the modulated imaging data set.

9. The method of claim 6, wherein mapping M odd echo data sets and M even echo data sets as the virtual imaging data set for the virtual coil array comprises:
mapping M modulated odd echo data sets and M modulated even echo data sets in the modulated imaging data sets as the virtual imaging data set for the virtual coil array.

10. The method of claim 1, wherein determining the odd echo phase information of the image data set by performing parallel magnetic resonance imaging based on the information associated with the receiving coil array and the odd echo data set in the imaging data set comprises:
determining an odd echo folding images for each of the N coil channels in the receiving coil array based on the odd echo data set in the imaging data set to obtain N odd echo folding images for the imaging data set;
obtaining an odd echo intermediate image for the imaging data set by performing Generalized Autocalibrating Partially Parallel Acquisitions (GRAPPA) parallel magnetic resonance imaging based on a convolution kernel for each of the N coil channels in the receiving coil array and the N odd echo folding images, wherein the information associate with the receiving coil array comprises the convolution kernel for each of the N coil channels in the receiving coil array;
obtaining a filtered odd echo intermediate image by performing low-pass filtering on the odd echo intermediate image for the imaging data set; and
extracting the odd echo phase information of the imaging data set from the filtered odd echo intermediate image.

11. The method of claim 1, wherein determining the even echo phase information of the image data set by performing parallel magnetic resonance imaging based on the information associated with the receiving coil array and the even echo data set in the imaging data set comprises:
determining an even echo folding image for each of the N coil channels in the receiving coil array based on the even echo data set in the imaging data set to obtain N even echo folding images for the imaging data set;
obtaining an even echo intermediate image for the imaging data set by performing Generalized Autocalibrating Partially Parallel Acquisitions (GRAPPA) parallel magnetic resonance imaging based on a convolution kernel for each of the N coil channels in the receiving coil array and the N even echo folding images, wherein the information associate with the receiving coil array comprises the convolution kernel for each of the N coil channels in the receiving coil array;
obtaining a filtered even echo intermediate image by performing low-pass filtering on the even echo intermediate image for the imaging data set; and
extracting the even echo phase information of the imaging data set from the filtered even echo intermediate image.

12. The method of claim 1, wherein performing parallel magnetic resonance imaging based on the odd echo phase information and the even echo phase information of each of the imaging data sets, the virtual imaging data set, and the parallel reconstruction reference data comprises:
determining a convolution kernel for each of the N coil channels in the receiving coil array based on the parallel reconstruction reference data comprising pre-collected partial K-space data;
determining a respective virtual convolution kernel for each of the N×M×2 virtual coil channels in the virtual coil array based on the convolution kernel for each of the N coil channels in the receiving coil array and the number M;
determining a reconstruction calculation factor of the virtual coil array based on the virtual convolution kernel for each of the N×M×2 virtual coil channels and the odd echo phase information and the even echo phase information in each of the imaging data sets;
determining a respective original folding image for each of the N×M×2 virtual coil channels in the virtual coil array based on the virtual imaging data set to obtain N×M×2 original folding images; and
performing Generalized Autocalibrating Partially Parallel Acquisitions (GRAPPA) parallel magnetic resonance imaging based on the reconstruction calculation factor of the virtual coil array and the N×M×2 original folding images.

13. A magnetic resonance imaging apparatus, comprising:
at least one processor; and
at least one non-transitory machine readable storage medium coupled to the at least one processor having machine-executable instructions stored thereon that, when executed by the at least one processor, cause the at least one processor to perform operations comprising:
obtaining M imaging data sets collected by a receiving coil array under M radio-frequency excitations, wherein the receiving coil array comprises N coil channels, the imaging data set obtained under each of the radio frequency excitations comprises an odd echo data set and an even echo data set, and N is an integer greater than 1;
for each of the imaging data sets,
determining odd echo phase information of the imaging data set by performing parallel magnetic resonance imaging based on information associated with the receiving coil array and the odd echo data set in the imaging data set;
determining even echo phase information of the imaging data set by performing parallel magnetic resonance imaging based on the information associated with the receiving coil array and the even echo data set in the imaging data set;
mapping M odd echo data sets and M even echo data sets as a virtual imaging data set for a virtual coil array, wherein the virtual coil array comprises N×M×2 virtual coil channels; and
performing parallel magnetic resonance imaging based on the odd echo phase information and the even echo phase information of each of the imaging data sets, the virtual imaging data set and parallel reconstruction reference data.

14. The apparatus of claim 13, wherein determining the odd echo phase information of the imaging data set by performing magnetic parallel resonance imaging based on the information associated with the receiving coil array and the odd echo data set in the imaging data set comprises:
determining an odd echo folding image for each of the N coil channels in the receiving coil array based on the odd echo data set in the imaging data set to obtain N odd echo folding images for the imaging data set;

obtaining an odd echo intermediate image for the imaging data set by performing Sensitivity Encoding (SENSE) parallel resonance imaging based on coil sensitivity information of the receiving coil array and the N odd echo folding images, wherein the information associated with the receiving coil array comprises the coil sensitivity information of the receiving coil array;

obtaining a filtered odd echo intermediate image by performing low-pass filtering on the odd echo intermediate image for the imaging data set; and extracting the odd echo phase information of the imaging data set from the filtered odd echo intermediate image.

15. The apparatus of claim 13, wherein determining the even echo phase information of the imaging data set by performing parallel magnetic resonance imaging based on the information associated with the receiving coil array and the even echo data set in the imaging data set comprises:

determining an even echo folding image for each of the N coil channels in the receiving coil array based on the even echo data set in the imaging data set to obtain N even echo folding images for the imaging data set;

obtaining an even echo intermediate image for the imaging data set by performing Sensitivity Encoding (SENSE) parallel magnetic resonance imaging based on coil sensitivity information of the receiving coil array and the N even echo folding images, wherein the information associated with the receiving coil array comprises the coil sensitivity information of the receiving coil array;

obtaining a filtered even echo intermediate image by performing low-pass filtering on the even echo intermediate image for the imaging data set; and extracting the even echo phase information of the imaging data set from the filtered even echo intermediate image.

16. The apparatus of claim 13, wherein performing parallel magnetic resonance imaging based on the odd echo phase information and the even echo phase information of each of the imaging data sets, the virtual imaging data set and the parallel reconstruction reference data comprises:

determining virtual coil sensitivity information of the virtual coil array based on the parallel reconstruction reference data and the number M, wherein the parallel reconstruction reference data comprises coil sensitivity information of the receiving coil array;

determining a reconstruction calculation factor of the virtual coil array based on the virtual coil sensitivity information of the virtual coil array and the odd echo phase information and the even echo phase information of each of the imaging data sets;

determining a respective original folding image for each of the N×M×2 virtual coil channels in the virtual coil array based on the virtual imaging data set to obtain N×M×2 original folding images; and performing SENSE parallel magnetic resonance imaging based on the reconstruction calculation factor of the virtual coil array and the N×M×2 original folding images.

17. The apparatus of claim 13, wherein obtaining the M imaging data sets collected by the receiving coil array under the M radio-frequency excitations comprises:

controlling magnetic resonance scanning for a subject based on an Echo Planar Imaging (EPI) sequence, wherein the EPI sequence comprises the M radio-frequency excitations; and obtaining the M imaging data sets collected by the receiving coil array.

18. The apparatus of claim 13, wherein determining the odd echo phase information of the image data set by performing parallel magnetic resonance imaging based on the information associated with the receiving coil array and the odd echo data set in the imaging data set comprises:

determining an odd echo folding images for each of the N coil channels in the receiving coil array based on the odd echo data set in the imaging data set to obtain N odd echo folding images for the imaging data set;

obtaining an odd echo intermediate image for the imaging data set by performing Generalized Autocalibrating Partially Parallel Acquisitions (GRAPPA) parallel magnetic resonance imaging based on a convolution kernel for each of the N coil channels in the receiving coil array and the N odd echo folding images, wherein the information associated with the receiving coil array comprises the convolution kernel for each of the N coil channels in the receiving coil array;

obtaining a filtered odd echo intermediate image by performing low-pass filtering on the odd echo intermediate image for the imaging data set; and extracting the odd echo phase information of the imaging data set from the filtered odd echo intermediate image.

19. The apparatus of claim 13, wherein determining the even echo phase information of the image data set by performing parallel magnetic resonance imaging based on the information associated with the receiving coil array and the even echo data set in the imaging data set comprises:

determining an even echo folding image for each of the N coil channels in the receiving coil array based on the even echo data set in the imaging data set to obtain N even echo folding images for the imaging data set;

obtaining an even echo intermediate image for the imaging data set by performing Generalized Autocalibrating Partially Parallel Acquisitions (GRAPPA) parallel magnetic resonance imaging based on a convolution kernel for each of the N coil channels in the receiving coil array and the N even echo folding images, wherein the information associated with the receiving coil array comprises the convolution kernel for each of the N coil channels in the receiving coil array;

obtaining a filtered even echo intermediate image by performing low-pass filtering on the even echo intermediate image for the imaging data set; and extracting the even echo phase information of the imaging data set from the filtered even echo intermediate image.

20. The apparatus of claim 13, wherein performing parallel magnetic resonance imaging based on the odd echo phase information and the even echo phase information of each of the imaging data sets, the virtual imaging data set, and the parallel reconstruction reference data comprises:

determining a convolution kernel for each of the coil channels in the receiving coil array based on the parallel reconstruction reference data comprising pre-collected partial K-space data;

determining a virtual convolution kernel for each of the N×M×2 virtual coil channels in the virtual coil array based on the convolution kernel for each of the N coil channels in the receiving coil array and the number M;

determining a reconstruction calculation factor of the virtual coil array based on the virtual convolution kernel for each of the N×M×2 virtual coil channel and the odd echo phase information and the even echo phase information in each of the imaging data sets;

determining a respective original folding image for each of the N×M×2 virtual coil channels in the virtual coil array based on the virtual imaging data set to obtain N×M×2 original folding images; and performing Generalized Autocalibrating Partially Parallel Acquisitions (GRAPPA) parallel magnetic resonance imaging based on the reconstruction calculation factor of the virtual coil array and the N×M×2 original folding images.

\* \* \* \* \*